US012582690B2

(12) United States Patent
Kwon et al.

(10) Patent No.: US 12,582,690 B2
(45) Date of Patent: Mar. 24, 2026

(54) **COMPOSITIONS FOR PREVENTING OR TREATING CANCER COMPRISING EXTRACTS OF *RUBUS LONGISEPALUS* VAR. *TOZAWAI* (NAKAI) T.B.LEE**

(71) Applicants: KOREA INSTITUTE OF SCIENCE AND TECHNOLOGY, Seoul (KR); INDUSTRY-ACADEMIC COOPERATION FOUNDATION, YONSEI UNIVERSITY, Seoul (KR)

(72) Inventors: Hak Cheol Kwon, Gangneung-si (KR); Jaeyoung Kwon, Gangneung-si (KR); Seong-Hwan Kim, Gangneung-si (KR); Jin Wook Cha, Gangneung-si (KR); Soon Kwang Lee, Gangneung-si (KR); Won Kyu Kim, Gangneung-si (KR); Yujin Kwon, Gangneung-si (KR); Suyeon Cho, Gangneung-si (KR); Taek Joo Lee, Yongin-si (KR); Jung Hwa Kang, Yongin-si (KR); Wan Hee Lee, Yongin-si (KR); Hyunki Kim, Goyang-si (KR)

(73) Assignees: Korea Institute of Science and Technology, Seoul (KR); Industry-Academic Cooperation Foundation, Yonsei University, Seoul (KR)

( * ) Notice: Subject to any disclaimer, the term of this patent is extended or adjusted under 35 U.S.C. 154(b) by 659 days.

(21) Appl. No.: 17/962,026

(22) Filed: Oct. 7, 2022

(65) Prior Publication Data

US 2023/0114565 A1 Apr. 13, 2023

(30) Foreign Application Priority Data

Oct. 8, 2021 (KR) ........................ 10-2021-0134448

(51) Int. Cl.
| | |
|---|---|
| *A61K 36/73* | (2006.01) |
| *A61K 36/268* | (2006.01) |
| *A61P 1/00* | (2006.01) |
| *A61P 35/00* | (2006.01) |

(52) U.S. Cl.
CPC ............ *A61K 36/73* (2013.01); *A61K 36/268* (2013.01); *A61P 1/00* (2018.01); *A61P 35/00* (2018.01); *A61K 2236/333* (2013.01); *A61K 2236/35* (2013.01); *A61K 2236/37* (2013.01)

(58) Field of Classification Search
CPC .. A61K 36/73; A61K 36/268; A61K 2236/37; A61K 2236/333; A61P 35/00; A61P 1/00
See application file for complete search history.

(56) References Cited

U.S. PATENT DOCUMENTS

2013/0115322 A1 5/2013 Stoner et al.

FOREIGN PATENT DOCUMENTS

| | | | |
|---|---|---|---|
| KR | 10-2007-0033236 A | | 3/2007 |
| KR | 10-1326162 B1 | | 11/2013 |
| KR | 10-2017-0045088 A | | 4/2017 |
| KR | 10-1924532 B1 | | 12/2018 |
| KR | 10-2020-0014633 A | | 2/2020 |
| KR | 10-2165171 B1 | | 10/2020 |
| WO | WO 2006/134609 A2 | | 12/2006 |

OTHER PUBLICATIONS

Assad et al. (Egypt. Acad. J. Biol. Sci., 7(20; 19-23 (2015).*
Kopyt'ko, Ya F., et al. "Medical Plants: Uses, Chemical Composition, and Standardization of Plant Raw Material and Medicinal Substances from Plants of the Genus *Asarum* L." *Pharmaceutical Chemistry Journal* vol. 47. Issue 3 (2013). pp 157-168.
Kim, Ok-Suk, et al. "Anti-proliferative effects of water extract of *Asarum sieboldii* in human cancer cells." *Cancer Prevention Research* (2006). pp 240-247.
Korean Office Action issued on Feb. 15, 2024, in counterpart Korean Patent Application No. 10-2021-0134448 (5 pages in English, 5 pages in Korean).

* cited by examiner

Primary Examiner — Shirley V Gembeh
(74) Attorney, Agent, or Firm — NSIP Law

(57) ABSTRACT

Provided are compositions for preventing or treating cancer, the compositions including *Rubus longisepalus* var. tozawai (Nakai) T.B.Lee extracts, or a fraction thereof as an active ingredient.

According to an aspect, a *Rubus longisepalus* var. tozawai (Nakai) T.B.Lee extract has an excellent anticancer efficacy against various cancers including diffuse-type gastric cancer, and thus, a cancer treatment agent having an excellent effect may be developed by using the extract as an active ingredient.

5 Claims, 10 Drawing Sheets

| NO. | sample name | NO. | sample name |
|---|---|---|---|
| 11 | Rubus longisepalus var. tozawai (Nakai) T.B.Lee Hexane fraction | 27 | Asarum maculatum Nakai BuOH fraction |

MKN1

□ 50    ▨ 100    ▨ 200(μg/ml)

SNU668

□ 50    ▨ 100    ▨ 200(μg/ml)

Normal Orgnoaid

1

COMPOSITIONS FOR PREVENTING OR TREATING CANCER COMPRISING EXTRACTS OF *RUBUS LONGISEPALUS* VAR. *TOZAWAI* (NAKAI) T.B.LEE

CROSS-REFERENCE TO RELATED APPLICATIONS

This application claims priority under 35 U.S.C. § 119 to Korean Patent Application No. 10-2021-0134448 filed on Oct. 8, 2021 in the Korean Intellectual Property Office, the disclosures of which are incorporated by reference herein in their entireties.

TECHNICAL FIELD

The present disclosure relates to compositions for preventing or treating cancer, the compositions including *Rubus longisepalus* var. tozawai (Nakai) T.B.Lee extracts, or a fraction thereof.

BACKGROUND

Despite advances in modern medicine, cancer is still one of the human diseases most difficult to treat. Cancer is a tissue composed of amassed abnormal cells that originate in one or more tissues and spread to other tissues. Currently, more than 100 types of cancer are known. It is known that the main cause of cancer is gene mutation caused by genetic and environmental factors. In the case of genetic factors, cancer is caused by mutated genes inherited from parents, and in the case of environmental factors, the factors include smoking, obesity, radiation, UV rays, stress, environmental pollution, and the like.

According to the statistics of Korean National Cancer Center in 2015, gastric cancer is the most common cancer among men and women in Korea. The incidence rate of cancer increases with age, but the incidence rate of cancer among young people is also increasing due to westernized eating habits and lack of exercise. In particular, gastric cancer ranks first among cancers in men in their 30s to 60s, and third among cancers in women of the same age group, after thyroid cancer and breast cancer, and is a disease that young people also need to be aware of. Gastric cancer is classified into an intestinal type and a diffuse type according to its shape. In the intestinal type, cancer cells gather in one place and grow in a lump, whereas in the diffuse type, tiny cancer cells penetrate the stomach wall and grow widely. This diffuse-type gastric cancer is more common in female patients, and is characterized by high malignancy and rapid progression. 'Diffuse-type gastric cancer' has been counted to account for about 35% to about 40% of all gastric cancer patients, and is more common among young people under the age of 40, and as described above, the risk of lymphatic metastasis is high and the prognosis is poor because the cancer infiltrates into the submucosa and grows without inflammation during the development process.

To date, treatment methods for cancer patients include surgical operation, chemotherapy, radiotherapy, target therapy, hormone therapy, and immunotherapy. Surgical operation, the surest radical means, is a treatment method of removing the lesion (that is, cancer). In the case of an early-stage cancer, the cancer may be completely cured with surgical operation only, however, in the case of a cancer after the middle stage, or in the case of organs which are difficult to access, there is a disadvantage in that it is impossible to use surgical operation at all. When surgical operation is not possible, most patients will be treated with drugs and radiation. Chemotherapy, radiation therapy, or a combination therapy thereof all in common removes target cancer cells by generating free radicals, and since the therapies have low specificity, normal cells with characteristics of rapid division and proliferation, such as hematopoietic cells or immune cells, are also damaged. Therefore, the therapies cause side effects such as vomiting, loss of appetite, stomatitis, diarrhea, constipation, fever, infection, leukopenia, thrombocytopenia, anemia, abdominal pain, kidney toxicity, liver toxicity, cardiac toxicity, peripheral neurotoxicity, central nervous system toxicity, muscle pain, bone pain, and bone marrow suppression. In order to minimize these side effects, targeted therapies have been used to inhibit cancer by recognizing a target such as a specific mutant protein, but cancer types in which targeted therapy is possible are very limited. In addition, recently, immunotherapy that removes cancer cells by inducing activation of immune cells has been in the spotlight, however, in reality, the patient group that responds to immunotherapy accounts for around 10% of all cancer patients. Also, it is difficult to use immunotherapy as an active treatment means due to the high price and absence of predictive biomarkers for drug reactivity.

Meanwhile, the development of anticancer drugs derived from a natural substance (for example, paclitaxel, vinblastine, camptothecin, etc.) has played an important role in effective cancer patient treatment. By extracting active ingredients from natural substances and developing them into medicines, natural medicines have been used as source materials for anticancer drugs for a long time. Most of the cytotoxic anticancer drugs that are frequently used in clinical practice to this day are derived from a natural substance or is a natural substance in which specific components are modified, and the development of anticancer drugs based on natural substances has played a key role in the history of anticancer drug development. Recently, in order to overcome the occurrence of side effects and resistance to anticancer drugs, and to secure diversity of anticancer drugs, various natural resources such as plants, marine organisms, and microorganisms have been developed as anticancer drug materials, and the importance of these drugs has been once again receiving attention.

Accordingly, the present inventors have prepared a composition including a *Rubus longisepalus* var. tozawai (Nakai) T.B.Lee extract, which is a natural substance, as an active ingredient. The composition may be used for a long period of time due to few side effects, and has excellent anticancer efficacy against diffuse-type gastric cancer, thereby solving the above problems.

DESCRIPTION OF EMBODIMENTS

Technical Problem

An aspect provides a pharmaceutical composition for preventing or treating cancer, the pharmaceutical composition including a *Rubus longisepalus* var. tozawai (Nakai) T.B.Lee extract or a fraction thereof as an active ingredient.

Another aspect provides a method of treating or preventing cancer, including administering the composition including a *Rubus longisepalus* var. tozawai (Nakai) T.B.Lee extract or a fraction thereof to a subject.

Still another aspect provides a food composition for preventing or improving cancer, the food composition including a *Rubus longisepalus* var. tozawai (Nakai) T.B.Lee extract or a fraction thereof as an active ingredient.

Still another aspect provides a feed composition for preventing or improving cancer, feed composition including a *Rubus longisepalus* var. tozawai (Nakai) T.B.Lee extract or a fraction thereof as an active ingredient.

Solution to Problem

An aspect provides a pharmaceutical composition for preventing or treating cancer, including a *Rubus longisepalus* var. tozawai (Nakai) T.B.Lee extract or a fraction thereof as an active ingredient.

The term "*Rubus tozawae* Nakai ex J.Y.Yang [*Rubus longisepalus* var. tozawai (Nakai) T.B.Lee]" used herein refers to a deciduous broad-leaved shrub that grows naturally at the foot of a seaside mountain, blooms in April, of which fruits ripen to yellow in June, and is known to be distributed in Yeosu-si, Jeollanam-do, Geoje-si, Gyeongsangnam-do, Jinhae, Tongyeong, and Seogwipo-si, Jeju-do. The leaves are often divided into 3 parts, have fine sawtooth on the edge, and have alternate phyllotaxy. *Rubus longisepalus* var. tozawai (Nakai) T.B.Lee resembles Mecdo strawberry (*Rubus longisepalus* Nakai), but the former is distinguished by having fine hairs and thorns on the petiole, and a short calyx piece.

The term "extract", used herein, may refer to a liquid component obtained by immersing a target substance in various solvents and then extracting the same at room temperature or in a heated state for a certain time, and may refer to a solid obtained by removing the solvent from the liquid component. In addition, the term may be comprehensively interpreted to include the extract itself and extracts of all formulations that may be formed by using the extract, such as a diluted solution, a concentrate, a crudely purified product, a purified product, or a mixture thereof.

The extract may be extracted from a natural, hybrid, or mutated plant of the corresponding plant, and may also be extracted from a plant tissue culture.

The extraction solvent of the extract may be a protic polar solvent or an aprotic polar and non-polar solvent. The protic polar solvent may be water, methanol, ethanol, propanol, isopropanol, or butanol. The aprotic polar solvent may be dichloromethane, tetrahydrofuran, ethyl acetate, acetonitrile, dimethylformamide, dimethylsulfoxide, acetone, 2-butanone, or hexamethylphosphoramide. The non-polar solvent may be pentane, hexane, chloroform, or diethylether. The non-polar solvent excludes benzene. The solvent may be a C1 to C6 alcohol, a C3 to C10 ester, for example, a C3 to C10 acetate, a C3 to C10 ketone, a C1 to C6 unsubstituted or halogenated hydrocarbon, a C2 to C10 cyclic ether, mixtures thereof, or a mixture of one or more of the above solvents and water. The solvent may be ethanol, propanol, acetonitrile, ethyl acetate, acetone, 2-butanone, chloroform, dichloromethane, hexane, a mixture thereof, or a mixture of at least one of the solvents and water. The hydrocarbon may be an alkane, alkene, or alkyne.

The extract may be one extracted with at least one solvent selected from water; C1 to C4 lower alcohols such as methanol, ethanol, propanol, and butanol; polyhydric alcohols such as glycerine, butylene glycol, and propylene glycol; and hydrocarbon solvents such as methyl acetate, ethyl acetate, acetone, benzene, hexane, diethyl ether, and dichloromethane.

The extract may be one extracted by at least one method selected from reduced pressure high temperature extraction, boiling extraction, reflux extraction, hot water extraction, cold extraction, room temperature extraction, ultrasonic extraction, steam extraction, and fractional extraction.

The term "fraction", used herein, refers to a resulting product obtained by performing fractionation in order to separate a specific component or a specific component group from a mixture including various components.

The fractionation method for obtaining the fraction is not particularly limited, and may be performed according to a method commonly used in the art. Non-limiting examples of the fractionation method include a fractionation method performed by treating various solvents, an ultrafiltration fractionation method performed by passing the sample through an ultrafiltration membrane having a constant molecular weight cut-off value, and a chromatographic fractionation method performing various chromatographies (prepared to separate particles according to their size, charge, hydrophobicity, or affinity), and combinations thereof.

The type of the fractionation solvent used to obtain the fraction is not particularly limited, and any solvent known in the art may be used. Non-limiting examples of the fractionation solvent include polar solvents such as water and alcohols having 1 to 4 carbon atoms; non-polar solvents such as hexane, ethyl acetate, chloroform, and dichloromethane; or a mixed solvent thereof. These may be used alone or in combination of one or more, but is not limited thereto.

The *Rubus longisepalus* var. tozawai (Nakai) T.B.Lee extract or a fraction thereof may be extracted or fractionated by using hexane as a solvent. In addition, the *Rubus longisepalus* var. tozawai (Nakai) T.B.Lee extract or a fraction thereof may be one extracted by using a solvent including at least one selected from water and alcohols having 1 to 4 carbon atoms, and fractionated from the extract by using n-hexane as a solvent.

The pharmaceutical composition may further include an *Asarum maculatum* Nakai extract or a fraction thereof, and specifically, may further include an *Asarum maculatum* Nakai butanol extract.

The term "*Asarum maculatum* Nakai", used herein, is a perennial plant belonging to the family Aristolochiaceae, which blooms in May and June, and is known to be distributed in Jeju, Jeonnam and Gyeongnam regions of Korea. Underground stems have distinct nodes and short internodes and are 3 mm to 4 mm in diameter. The fibrous roots develop in the internodes, have a diameter of about 1 mm, and are generated especially at the end of an underground stem. The leaves have alternate phyllotaxy, are deciduous, and the leaf body is broad heart-shaped, thick, dark green with clear white spots on the surface, and is 7 cm to 8 cm long, and 6 cm to 7 cm wide. This species is endemic to Korea, and it differs from the unpatterned *Asarum sieboldii* Miq. and *Asarum* mandshuricum in that the leaves are thicker, and there is a white pattern on the front side of the leaf.

The *Asarum maculatum* Nakai extract or a fraction thereof may be extracted or fractionated with at least one solvent selected from hexane and butanol, specifically, may be extracted or fractionated with butanol as a solvent. In addition, the *Asarum maculatum* Nakai extract or a fraction thereof may be extracted by using a solvent including at least one selected from water and alcohols having 1 to 4 carbon atoms, and fractionated from the extract by using at least one solvent selected from hexane and n-butanol.

The term "cancer", used herein, refers to a tumor that has grown abnormally by uncontrolled excessive growth of body tissues, or a disease that forms a tumor. The cancer may be gastric cancer (intestinal-type gastric cancer, diffuse-type gastric cancer), liver cancer, lung cancer, pancreatic cancer, non-small cell lung cancer, colon cancer, bone cancer, skin cancer, head or neck cancer, skin or intraocular melanoma, uterine cancer, ovarian cancer, rectal cancer, colorectal cancer, perianal cancer, colon cancer, breast cancer, cervical cancer, fallopian tube carcinoma, endometrial carcinoma, vaginal carcinoma, vulvar carcinoma, Hodgkin's disease, esophageal cancer, small intestine cancer, adenocarcinoma of endocrine glands, thyroid cancer, parathyroid cancer, adrenal cancer, soft tissue sarcoma, urethral cancer, penile cancer, prostate cancer, chronic or acute leukemia, lymphocytic lymphoma, bladder cancer, kidney or ureter cancer, renal cell carcinoma, renal pelvic carcinoma, central nervous system (CNS) tumor, primary central nervous system lymphoma, spinal cord tumor, brainstem glioma, or pituitary adenoma, specifically, diffuse-type gastric cancer.

The term "diffuse-type gastric cancer", used herein, refers to a type of gastric cancer, which is a cancer that infiltrates through and grows under the gastric mucosa that does not form lumps, but may develop as small cancer cells spread throughout the stomach. Gastric cancer may be classified into an intestinal type and a diffuse type by a histological classification method. Compared to the intestinal type, in which the cancer grows in a lump on the mucosal surface and the growth rate is slow, the diffuse type metastasizes quickly, and in most cases, is worsened to stage 3 or 4 at the time of diagnosis. In general, gastric cancer commonly occurs in elderly men clinically and pathologically and has a strong epidemiologic correlation with *Helicobacter pylori* infection, on the other hand, diffuse-type gastric cancer is relatively dominant in women and young people, the cause of its occurrence is unknown, and it is known that the results of anticancer treatment are worse than those of intestinal-type gastric cancer.

The term "treatment", used herein, refers to any action that improves or beneficially changes the symptoms of cancer by administration of the composition of the present disclosure.

The term "prevention", used herein, refers to any action that suppresses or delays cancer or a possibility of an onset of the disease by administration of the composition of the present disclosure.

The *Rubus longisepalus* var. tozawai (Nakai) T.B.Lee extract or a fraction thereof has a cancer cell growth inhibitory effect, such as inducing cell death of cancer cells and/or inhibiting cell proliferation of cancer cells, thereby may effectively treat/improve or prevent cancer.

The pharmaceutical composition may include a pharmaceutically acceptable carrier. The "pharmaceutically acceptable carrier" may mean a carrier or a diluent that does not inhibit the biological activity and properties of the injected compound d without irritating the organism. Herein, "pharmaceutically acceptable" means not inhibiting the activity of the active ingredient and not having more toxicity than the application (administration) target is capable of adapting to. The carrier that may be used in the pharmaceutical composition may be any carrier that is commonly used in the art and pharmaceutically acceptable. Non-limiting examples of the carrier include lactose, dextrose, maltodextrin, sucrose, sorbitol, mannitol, xylitol, erythritol, maltitol, glycerol, ethanol, starch, acacia gum, alginate, gelatin, calcium phosphate, calcium silicate, cellulose, methyl cellulose, microcrystalline cellulose, polyvinyl pyrrolidone, water, saline, sterile water, Ringer's solution, buffered saline, albumin injection solution, methylhydroxybenzoate, propylhydroxybenzoate, talc, magnesium stearate, mineral oil, etc. These may be used alone or may be used in combination of two or more. The pharmaceutical composition may be prepared as an oral dosage formulation or a parenteral dosage formulation including a pharmaceutically acceptable carrier in addition to the active ingredient, according to a route of administration by a method known in the art. The pharmaceutical composition may be formulated as oral formulations, such as powders, granules, tablets, capsules, suspensions, emulsions, syrups, aerosols, etc., external preparations, suppositories, or sterile injection solutions each according to a method in the art.

When formulating the pharmaceutical composition, a generally used diluent or excipient such as a filler, an extender, a binder, a wetting agent, a disintegrant, or a surfactant may be used, but is not be limited thereto.

When the pharmaceutical composition is prepared as an oral dosage formulation, the pharmaceutical composition may be prepared as formulations such as powders, granules, tablets, pills, sugarcoated pills, capsules, liquids, gels, syrups, suspensions, emulsions, aerosols, wafers, and the like, together with a suitable carrier according to a method known in the art. In this regard, examples of pharmaceutically acceptable and suitable carriers include sugars such as lactose, glucose, sucrose, dextrose, sorbitol, mannitol, and xylitol, starches such as corn starch, potato starch, wheat starch, celluloses, such as cellulose, methylcellulose, ethylcellulose, sodium carboxymethylcellulose, and hydroxypropylmethylcellulose, polyvinylpyrrolidone, water, methylhydroxybenzoate, propylhydroxybenzoate, magnesium stearate, mineral oil, malt, gelatin, talc, polyol, vegetable oil, etc. The formulation may be prepared by using a diluent and/or excipient such as a filler, an extender, a binder, a wetting agent, a disintegrant, or a surfactant.

When the pharmaceutical composition is prepared as a parenteral formulation, the pharmaceutical composition may be formulated in the form of injections, transdermal administrative agents, nasal inhalants and suppositories, together with a suitable carrier according to a method known in the art. In the case of a formulation for injection, suitable carriers include sterile water, ethanol, polyols such as glycerol or propylene glycol, or a mixture thereof, preferably, Ringer's solution, phosphate buffered saline (PBS) containing triethanolamine, sterile water for injection, an isotonic solution such as 5% dextrose may be used. When formulated for transdermal administration, the pharmaceutical formulation may be formulated in the form of an ointment, a cream, a lotion, a gel, an external solution, a paste, a liniment, or an air lozenge. In the case of nasal inhalants, the pharmaceutical formulation may be formulated in the form of an aerosol spray by using a suitable propellant such as dichlorofluoromethane, trichlorofluoromethane, dichlorotetrafluoroethane, carbon dioxide, and the like. When the pharmaceutical formulation is formulated as a suppository, witepsol, tween 61, polyethyleneglycols, cacao fat, laurin, polyoxyethylene sorbitan fatty acid esters, polyoxyethylene stearate, sorbitan fatty acid esters and the like may be used as a base.

The pharmaceutical composition may be administered in a pharmaceutically effective amount. The term "pharmaceutically effective amount" means an amount sufficient to treat or prevent a disease with a reasonable benefit/risk ratio applicable to medical treatment or prevention, and an effective dose level may be determined depending on the severity of the disease, the activity of the drug, the patient's age, weight, health, and sex, the patient's sensitivity to the drug, the time of administration of the composition of the present disclosure used, the route of administration and the rate of excretion, the duration of treatment, and factors including the drug used in combination or concurrently used with the composition of the present disclosure, and other factors well known in the medical field. The pharmaceutical composition of the present disclosure may be administered alone or in combination with a component known to exhibit therapeutic effects on known cancers. Taking all of the above factors into consideration, it is important to administer an amount capable of obtaining the maximum effect with a minimum amount without side effects.

The dosage of the pharmaceutical composition may be determined by those skilled in the art in consideration of the purpose of use, the severity of the disease, the patient's age, weight, sex, and medical history, or the type of the substance used as an active ingredient. For example, the pharmaceutical composition of the present disclosure may be administered to an adult in an amount of about 0.1 ng/kg to about 1,000 mg/kg, preferably, about 1 ng/kg to about 100 mg/kg. The composition may be administered once a day or administered several times in aliquots, although administration frequency of the composition of the present disclosure is particularly limited thereto. The dosage or frequency of administration is not intended to limit the scope of the present application in any way.

Another aspect provides a method of treating or preventing cancer, including administering the pharmaceutical composition including a *Rubus longisepalus* var. tozawai (Nakai) T.B.Lee extract or a fraction thereof to a subject. The same parts as those described above are equally applied to the above method.

The term "subject", used herein, may include mammals including dogs, cats, mice, livestock, humans, etc., birds, reptiles, farmed fish, etc., which have developed cancer or are at risk of developing cancer.

The pharmaceutical composition may further include an *Asarum maculatum* Nakai extract or a fraction thereof, and specifically, may further include an *Asarum maculatum* Nakai butanol extract.

The pharmaceutical composition may be administered once or multiple times in a pharmaceutically effective amount. In this regard, the composition may be formulated and administered in the form of, for example, a liquid, a powder, an aerosol, an injection, a solution for intravenous infusion, a capsule, a pill, a tablet, a suppository, or a patch. The pharmaceutical composition for preventing or treating cancer may be administered through any general route as long as the composition can reach the target tissue.

The pharmaceutical composition may be administered through intraperitoneal administration, intravenous administration, intramuscular administration, subcutaneous administration, intradermal administration, transdermal patch administration, oral administration, intranasal administration, intrapulmonary administration, rectal administration, etc., according to the purpose of administration, but is not particularly limited thereto. However, when administered orally, the pharmaceutical composition may be administered in an unformulated form, or since the active ingredient of the pharmaceutical composition may be denatured or degraded by gastric acid, the composition for an oral administration may be administered in a form in which the active agent is coated, or the composition is formulated to protect the active agent from degradation in the stomach, or in a form of an oral patch. In addition, the composition may be administered by any device capable of transporting the active substance to the target cell.

Still another aspect provides a feed composition for preventing or improving cancer, including a *Rubus longisepalus* var. tozawai (Nakai) T.B.Lee extract or a fraction thereof as an active ingredient. The same parts as those described above are equally applied to the composition.

The term "improvement", used herein, refers to any action that improves or beneficially changes the symptoms of cancer by administration of the composition of the present disclosure.

The term "food", used herein, refers to meat, sausages, bread, chocolates, candies, snacks, confectionery, pizza, ramen, other noodles, gums, dairy products including ice cream, various soups, beverages, tea, drinks, alcoholic beverages, vitamin complexes, health functional foods, and health foods, and includes all foods in a conventional sense.

The food may be prepared by a method commonly used in the art, and at the time of manufacture, it may be prepared by adding raw materials and components commonly added in the art. In addition, the formulation of the food may be prepared without limitation as long as it is a formulation recognized as a food. The food composition may be prepared in various forms, and since food is the raw material unlike general drugs, it has an advantage of not having side effects that may occur during long-term administration of drugs, and has excellent portability, so the food composition of the present disclosure may be taken as an adjuvant for enhancing the effect of improving cancer.

The food composition may be a health functional food composition.

The term "health functional food", used herein, refers to food manufactured and processed using raw materials or ingredients having functionality useful for the human body according to the Health Functional Food Act No. 6727, and the term "functionality" refers to obtaining useful effects for health purposes, such as regulating nutrients or having physiological effects for the structure and function of the human body.

The "health food" means a food having an effect of active health maintenance or promotion compared to general food, and the "health supplement food" means a food for the purpose of supplementing health. In some cases, the terms health functional food, health food, and health supplement food may be used interchangeably. Specifically, the health functional food means food prepared by adding the composition to food materials such as beverages, teas, spices, gums, and confectionery, or food prepared as a capsule, powder, a suspension, etc., which may bring about certain health effects when ingested, however, unlike general drugs, health functional food has the advantage that there are no side effects that may occur when taking a drug for a long time because food is used as the raw material.

Since the food composition may be consumed on a daily basis, the food composition may be expected to be highly effective in the improvement of cancer, and may be very useful.

The food composition may further include a physiologically acceptable carrier, whrerein a type of the carrier is not particularly limited and any carrier commonly used in the art may be used. Specifically, the food composition may include additional ingredients that are commonly used in food compositions to improve odor, taste, vision, and the like. For example, vitamins A, C, D, E, B1, B2, B6, B12, niacin, biotin, folate, pantothenic acid, and the like may be included. Also, minerals such as zinc (Zn), iron (Fe), calcium (Ca), chromium (Cr), magnesium (Mg), manganese (Mn), and copper (Cu) may be included. In addition, amino acids such as lysine, tryptophan, cysteine, and valine may be included.

In addition, the food composition may include food additives such as preservatives (potassium sorbate, sodium benzoate, salicylic acid, sodium dehydroacetate, etc.), disinfectants (bleaching powder and high bleaching powder, sodium hypochlorite, etc.), antioxidants (butylhydroxyanisole (BHA), butylhydro oxytoluene (BHT), etc.), coloring agents (tar pigment, etc.), color developers (sodium nitrite, etc.), bleaches (sodium sulfite), seasonings (monosodium glutamate (MSG), etc.), sweeteners (dulcin, cyclimate, saccharin, sodium, etc.), flavorings (vanillin, lactones, etc.), leavening agents (alum, D-potassium hydrogen tartrate, etc.), strengthening agents, emulsifying agents, thickening agents (thickener), coating agents, gum base agents, antifoaming agents, solvents, and improving agents. The additives may be selected according to a type of food and used in an appropriate amount.

The food composition may be added as it is or used together with other foods or food ingredients, and may be appropriately used according to a method in the art. The mixed amount of the active ingredient may be suitably determined according to the purpose of its use (prevention, health, or therapeutic treatment). In general, when preparing food or beverage, the food composition of the present disclosure may be added in an amount of 50 parts by weight or less, specifically, 20 parts by weight or less with respect to the food or beverage. However, when consumed for a long period of time for health and hygiene purposes, the food composition may contain an amount less than the above range, and since there is no problem in terms of safety, the active ingredient may be used in an amount exceeding the above range.

As an example of the food composition, the food composition may be used as a health drink composition, and in this regard, the health drink composition may contain various flavoring agents or natural carbohydrates as additional components like a drink in the art. The above-described natural carbohydrates include monosaccharides such as glucose and fructose; disaccharides such as maltose and sucrose; polysaccharides such as dextrin and cyclodextrin; or a sugar alcohol such as xylitol, sorbitol, or erythritol. The sweeteners include natural sweeteners such as taumatine, *stevia* extract; or synthetic sweeteners such as saccharin, or aspartame. The ratio of the natural carbohydrate may be about 0.01 g to about 0.04 g, specifically, about 0.02 g to about 0.03 g per 100 mL of the health beverage composition of the present disclosure.

In addition to the above, the health beverage composition may include various nutrients, vitamins, electrolytes, flavoring agents, colorants, pectic acid, salts of pectic acid, alginic acid, salts of alginic acid, organic acids, protective colloidal thickeners, pH adjusters, stabilizers, preservatives, glycerin, alcohol, carbonating agents, and the like. In addition, the health beverage composition may contain pulp for production of natural fruit juice, fruit juice beverage, or vegetable beverage. These components may be used independently or in combination. Although the ratio of these additives is not very important, it is generally selected in the range of 0.01 parts by weight to 0.1 parts by weight per 100 parts by weight of the health beverage composition of the present disclosure.

The food composition may include the extract of the present disclosure in various wt % within the range that the food composition can exhibit an effect of improving or preventing cancer, specifically, 0.00001 wt % to 100 wt % or 0.01 wt % to 80 wt % with respect to the total weight of the food composition, but is not limited thereto.

Still another aspect is to provide a feed composition for preventing or improving cancer, including a *Rubus longisepalus* var. tozawai (Nakai) T.B.Lee extract or a fraction thereof as an active ingredient. The same parts as those described above are equally applied to the composition.

The term "feed", used herein, may refer to any natural or artificial diet, a meal, or components of the meal, for, or suitable for an animal to eat, ingest, and digest.

The type of feed is not particularly limited, and feed commonly used in the art may be used. Non-limiting examples of the feed include plant feeds such as grains, root fruits, food processing by-products, algae, fibers, pharmaceutical by-products, oils and fats, starches, gourds or grain by-products; and animal feeds such as proteins, inorganic materials, oils and fats, minerals, single cell proteins, zooplankton, or food. These may be used alone or may be used in combination of two or more.

The feed composition may further include known additives that may be added to improve or prevent cancer depending on the formulation. The feed composition may be in a form of a highly concentrated solution, powder or granules. The feed composition may further include any protein-containing organic grain flour commonly used to meet dietary needs of animals. The feed composition may be used by adding the same to animal feed by dipping, spraying, or mixing.

The feed composition may further include substances exhibiting various effects, such as nutrient supplementation and weight loss prevention, enhancement of digestibility of fiber in feed, improvement of oil quality, prevention of reproductive disorders and improvement of fertility, prevention of high temperature stress in summer. For example, mineral preparations such as sodium bicarbonate, bentonite, magnesium oxide, and complex minerals, trace minerals such as zinc, copper, cobalt, selenium, vitamins such as carotene, vitamin E, vitamins A, D, E, nicotinic acid, and vitamin B complex, protective amino acids such as methionine and lysine, protective fatty acids such as fatty acid calcium salt, live bacteria such as probiotics (lactic acid bacteria), yeast cultures, mold fermented products, yeast agents, etc. may be included.

The feed composition may be applied to a number of animal diets including diets for mammals and poultry, that is, in feed and drinking water.

The feed composition may include all of the material added to the feed (that is, feed additives), a feed raw material, or the feed itself fed to a subject.

Advantageous Effects of Disclosure

According to an aspect, a *Rubus longisepalus* var. tozawai (Nakai) T.B.Lee extract has an excellent anticancer efficacy against various cancers including diffuse-type gastric cancer, and a cancer treatment agent having an excellent effect may be developed by using the extract as an active ingredient.

BRIEF DESCRIPTION OF THE FIGURES

The above and other aspects, features, and advantages of certain embodiments of the disclosure will be more apparent from the following description taken in conjunction with the accompanying drawings, in which.

DETAILED DESCRIPTION

Figure 1:
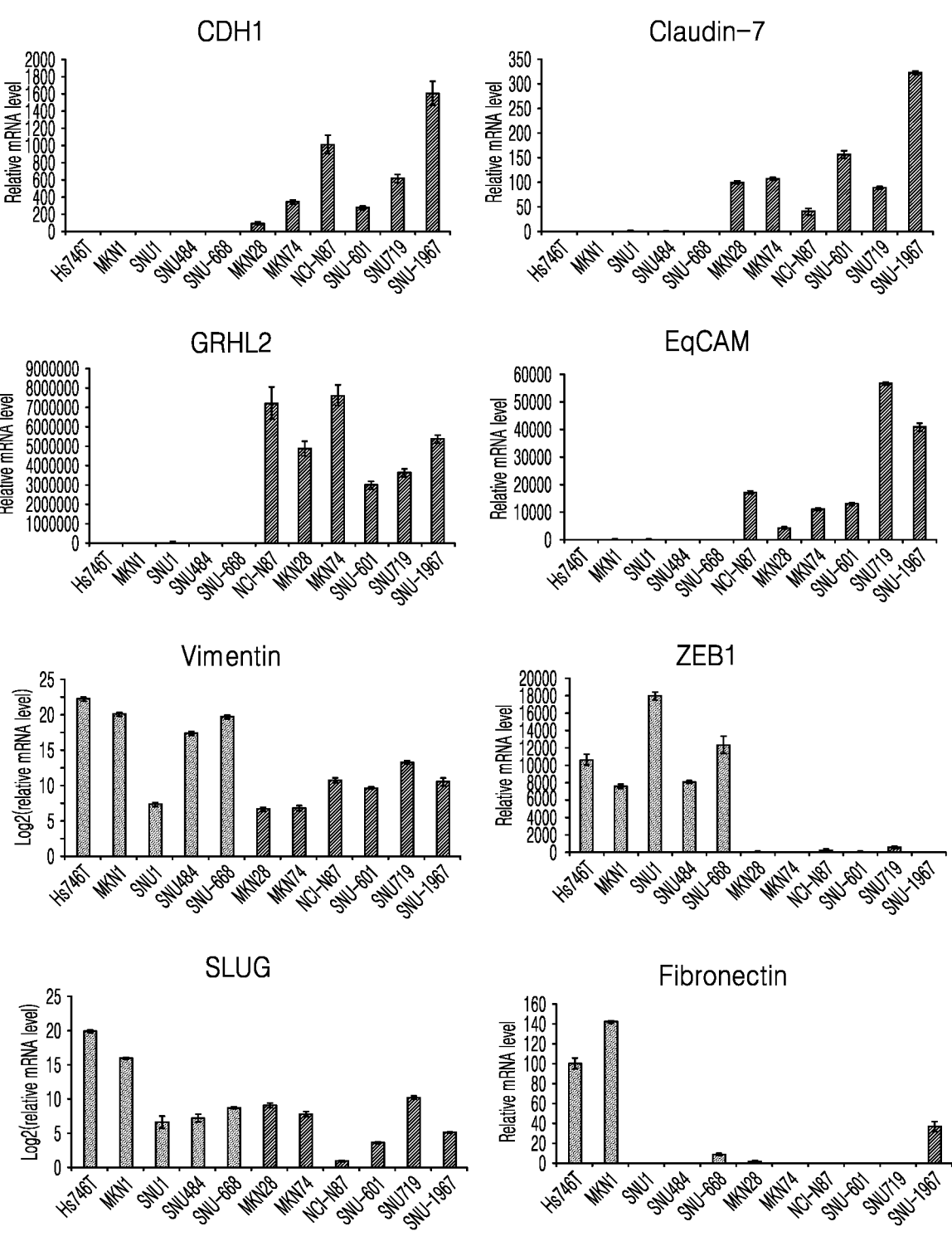
FIG. 1 shows diagrams for measuring expression levels of markers related to epithelial-mesenchymal transition for screening for diffuse-type gastric cancer cell lines.

Reference will now be made in detail to embodiments, embodiments of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of at least one of the associated listed items. Expressions such as "at least one of," when preceding a list of elements, modify the entire list of elements and do not modify the individual elements of the list.

Hereinafter, the present disclosure will be described in more detail through examples. However, these examples are intended to illustrate the present disclosure, and the scope of the present disclosure is not limited to these examples.

Example 1: Establishment of Diffuse-Type Gastric Cancer Cell Models

The following experiment was performed in order to establish diffuse-type gastric cancer cell models for screening for effective substances for treating diffuse-type gastric cancer.

Specifically, in order to select diffuse-type gastric cancer cell lines, epithelial mesenchymal transition levels of 11 gastric cancer cell lines (Hs746T, MKN1, SNU1, SNU-668, MKN28, MKN74, NCI-N87, SNU-601, SNU-719, SNU-1967) were measured. To this end, after culturing the cells, mRNA expression levels of 8 markers (CDH1, Claudin-7, GRHL2, EpCAM, Vimentin, ZEB1, SLUG, Fibronectin), which may confirm the degree of epithelial-mesenchymal transition, were confirmed (FIG. 1).

As a result, among cell lines with low expression levels of CDH1, Claudin-7, GRHL2, and EpCAM and high expression levels of Vimentin, ZEB1, SLUG, and Fibronectin, MKN1 and SNU668 were selected as diffuse-type gastric cancer cell lines. In the following examples, substances for treating diffuse-type gastric cancer were screened by using the cell lines.

Example 2: Screening for Active Substances for Treating Diffuse-Type Gastric Cancer In order to screen for effective substances for treating diffuse-type gastric cancer from various natural products, the following experiments were performed.

A 3-[4,5-dimethylthiazol-2-yl]-2,5 diphenyl tetrazolium bromide (MTT) assay was performed to evaluate cell growth inhibitory ability according to treatment of samples of natural extracts. Specifically, each cell line was seeded in a 96-well plate by 5000 each and cultured for one day, then, the experimental groups were treated with samples of each concentration, incubated for 72 hours, and 50 μL of MTT (2 mg/mL) dye was added. Thereafter, additional incubation was performed for 4 hours, the medium was removed, and dimethyl sulfoxide was added to each well to dissolve the dye for 20 minutes, and then absorbance was measured at a wavelength of 490 nm to analyze the degree of cell viability.

Figure 2:
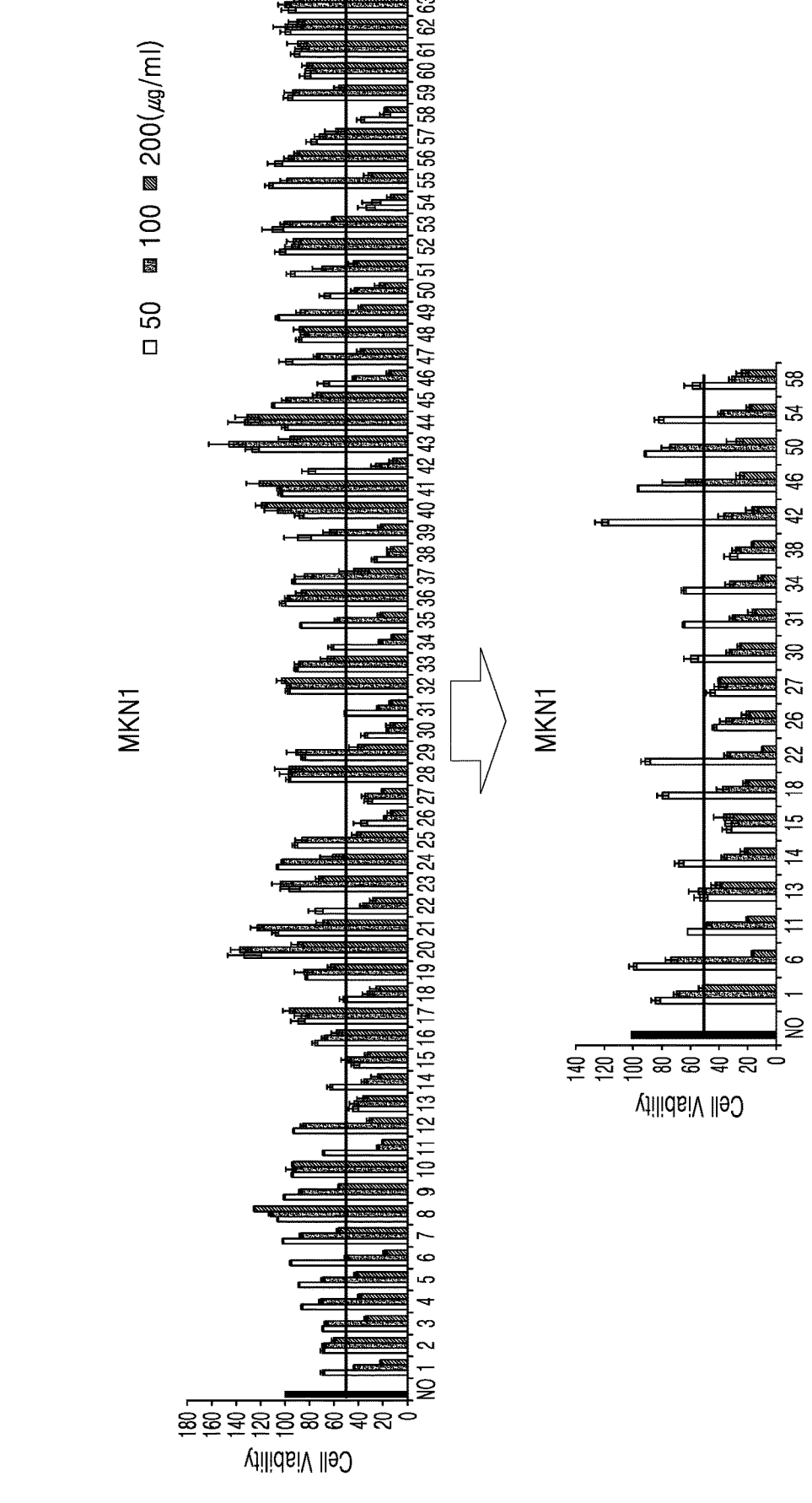
FIG. 2 shows a diagram showing results of a primary screening for selecting candidate active substances for treating diffuse-type gastric cancer.
Figure 3:
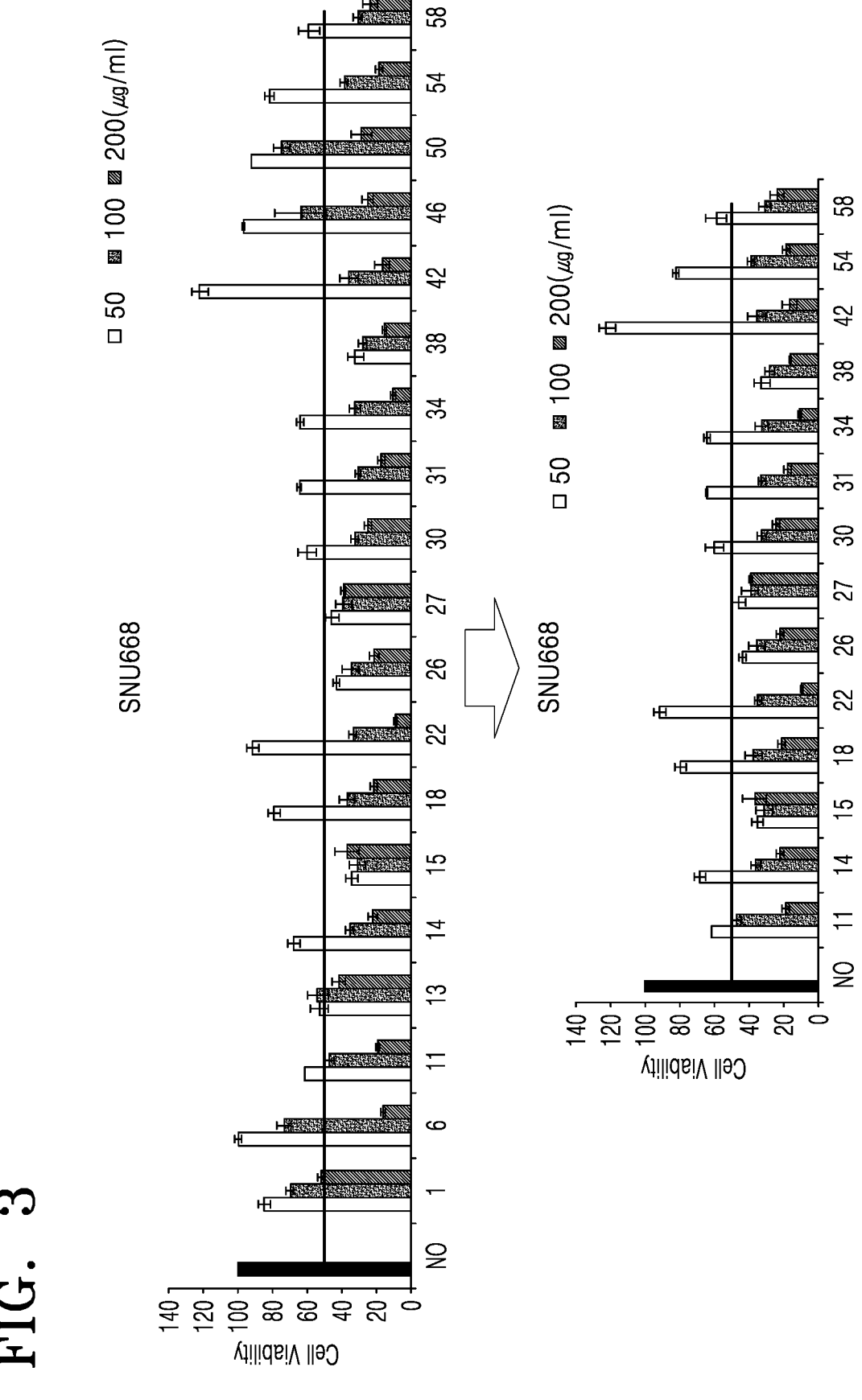
FIG. 3 shows a diagram showing results of a secondary screening for selecting candidate active substances for treating diffuse-type gastric cancer.

First, for a primary screening, after 63 kinds of natural substance extract samples of each concentration (50 μg/ml, 100 μg/ml, and 200 μg/ml) were treated to MKN1, a diffuse-type gastric cancer cell line selected in Example 1, cell growth inhibitory ability was confirmed by an MTT assay, and samples showing 50% or more cell growth inhibitory activity when treated at a concentration of 100 μg/ml were primarily selected. As a result, it was confirmed that 19 samples out of a total of 63 samples exhibited 50% or more of cell growth inhibitory activity against MKN1, and the 19 samples were primarily selected (FIG. 2).

Next, for a secondary screening, after 19 kinds of primarily selected natural substance extract samples of each concentration (50 μg/ml, 100 μg/ml, and 200 μg/ml) were treated to SNU688, a diffuse-type gastric cancer cell line selected in Example 1, cell growth inhibitory ability was confirmed by an MTT assay, and samples showing 50% or more cell growth inhibitory activity when treated at a concentration of 100 μg/ml were secondarily selected. As a result, it was confirmed that 14 samples out of a total of 19 samples exhibited 50% or more of cell growth inhibitory activity against SNU688, and the 14 samples were secondarily selected (FIG. 2).

Figure 4:
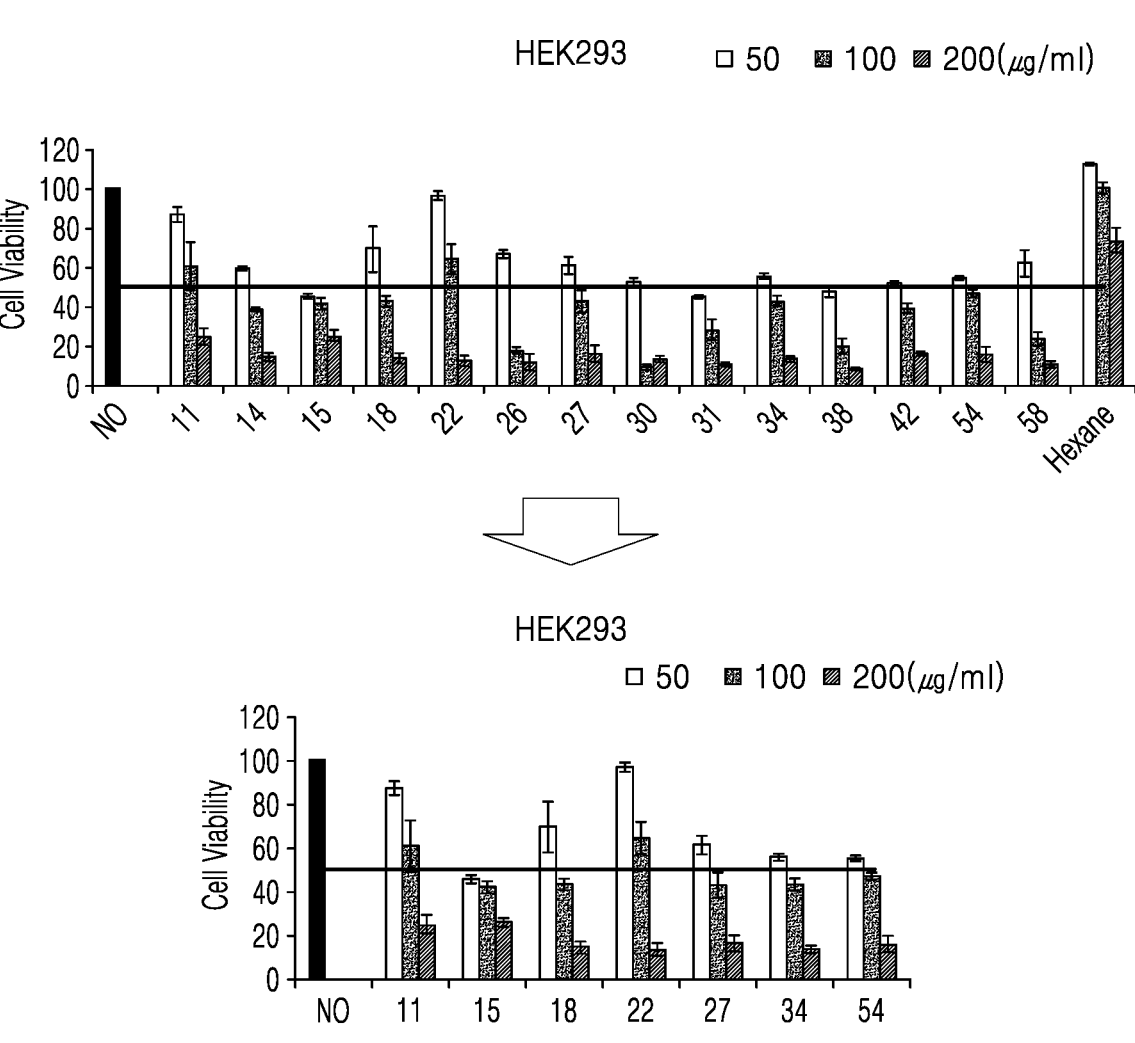
FIG. 4 shows a diagram showing results of a tertiary screening for selecting candidate active substances for treating diffuse-type gastric cancer.

Next, for a tertiary screening based on cytotoxicity on normal cells, after 14 kinds of secondarily selected natural substance extract samples of each concentration (50 μg/ml, 100 μg/ml, and 200 μg/ml) were treated to HEK293, a normal cell line, cell viability inhibitory ability on normal cells was confirmed by an MTT assay, and samples showing 45% to 50% or less cell viability inhibitory activity when treated at a concentration of 100 μg/ml were tertiary selected. As a result, it was confirmed that 7 samples out of a total of 14 samples exhibited less than about 45% to about 50% of normal cell viability inhibitory activity on HEK293, and the 7 samples with low toxicity to normal cell lines were tertiary selected (FIG. 4).

In addition, by comprehensively considering the inhibitory activity on MKN1 and SNU668, which are diffuse-type gastric cancer cell lines, and the cytotoxicity results for a normal cell line, a *Rubus tozawae* Nakai ex J.Y. Yang [*Rubus longisepalus* var. tozawai (Nakai) T.B.Lee] extract and an

*Asarum maculatum* Nakai extract were finally selected as candidate active substances for treating diffuse-type gastric cancer.

Example 3: Evaluation of Anticancer Efficacy of *Rubus Longisepalus* Var. Tozawai (Nakai) T.B.Lee Extract In order to evaluate anticancer efficacy of a *Rubus longisepalus* var. tozawai (Nakai) T.B.Lee extract selected as a candidate active substance for treating diffuse-type gastric cancer in Example 2, the following experiment was performed.

3.1 Preparation of *Rubus longisepalus* var. tozawai (Nakai) T.B.Lee Extract

In order to prepare an extract of *Rubus longisepalus* var. tozawai (Nakai) T.B.Lee by using various solvents, the following experiment was performed.

Specifically, whole plants of *Rubus longisepalus* var. tozawai were collected from Geoje Island in August 2020, washed with water sufficiently, and dried with warm air (30° C.) for 7 days to obtain 7.4 kg of dried plant. Thereafter, the dried plant was placed in a crusher and sliced to a size of 20 mm, and put into an extraction container, 74 L of 70% ethanol/water was added, the sample was stirred by shaking at room temperature for 7 days for an extraction, the process of gravity filtration by using a Whatman filter paper having a film thickness of 0.34 mm and a glass funnel was repeated twice ('extraction-filtration' twice) on the mixture to obtain a filtered extract. The filtered extract was transferred to a round flask, put in a low pressure evaporator, and concentrated by evaporating the solvent completely at 35° C. under reduced pressure to obtain 400 g of an ethanol extract of *Rubus longisepalus* var. tozawai (Nakai) T.B.Lee (yield 5.4%).

Next, 350 g of the *Rubus longisepalus* var. tozawai (Nakai) T.B.Lee ethanol extract was suspended in 4 L of water, 4 L of n-hexane was added, and the mixture was stirred by shaking at room temperature and fractionated 3 times for 2 hours each, to obtain 14 g of n-hexane fraction extract. After the fractionation, 4 L of water-saturated n-butanol was added to the remaining water, the mixture was stirred by shaking at room temperature, and fractionation was carried out 3 times for 2 hours each, to obtain 260 g of n-butanol fraction extract, and the water remaining after the fractionation was freeze-dried to obtain a water fraction extract.

3.2 Evaluation of Treatment Efficacy for Diffuse-Type Gastric Cancer for Each Extraction Solvent The following experiments were performed to evaluate a treatment efficacy for diffuse-type gastric cancer and cytotoxicity on cells of the *Rubus longisepalus* var. tozawai (Nakai) T.B.Lee extract prepared in Example 3.1 for each solvent.

Figure 5:
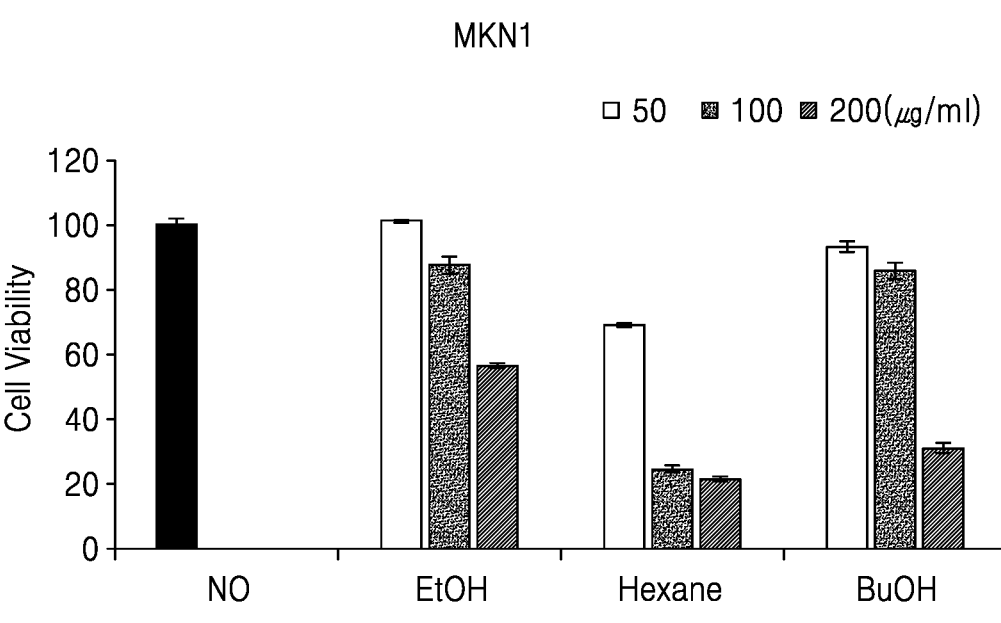
FIG. 5 shows diagrams confirming cell growth inhibitory ability of *Rubus longisepalus* var. tozawai (Nakai) T.B.Lee extracts for each solvent on diffuse-type gastric cancer cell lines.
Figure 5:
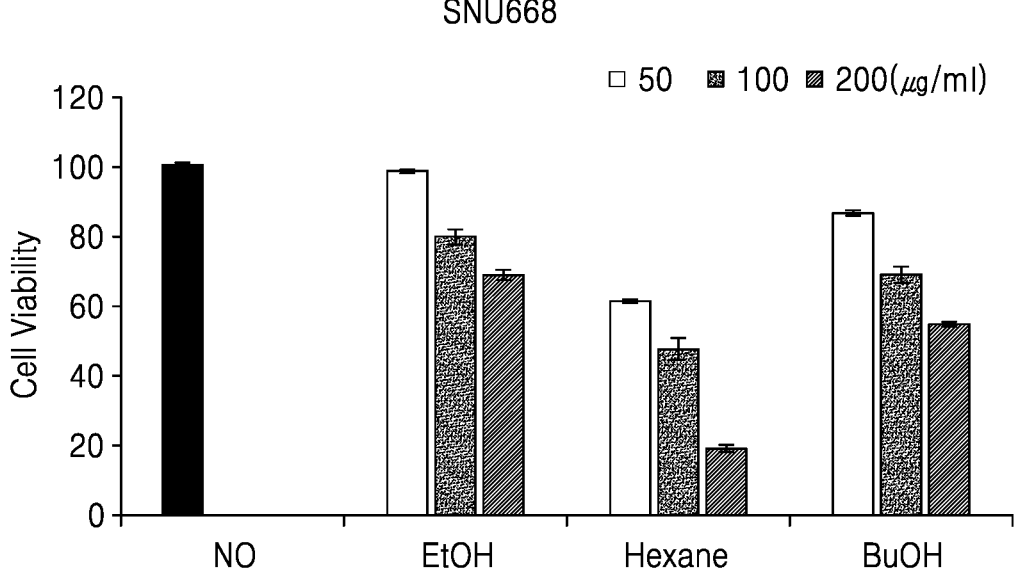

First, in order to evaluate anticancer efficacy against diffuse-type gastric cancer, *Rubus longisepalus* var. tozawai (Nakai) T.B.Lee extracts of each concentration (50 µg/ml, 100 µg/ml, and 200 µg/ml) for each solvent were treated on MKN1 and SNU668, which are the diffuse-type gastric cancer cell lines selected in Example 1, and then the cell growth inhibitory ability was confirmed by an MTT assay. As a result, it was confirmed that the hexane extract exhibited excellent anticancer efficacy against the two types of diffuse-type gastric cancer cell lines (FIG. 5).

Based on the above results, it may be seen that an hexane extract of *Rubus longisepalus* var. tozawai (Nakai) T.B.Lee, which has an excellent cell death effect for diffuse-type gastric cancer, has significantly superior anticancer efficacy among extracts for each solvent.

3.3 Evaluation of Treatment Efficacy for Diffuse-Type Gastric Cancer and Cytotoxicity of *Rubus longisepalus* Var. Tozawai (Nakai) T.B.Lee Hexane Extract-Cell Models The following experiments were performed to evaluate a treatment efficacy for diffuse-type gastric cancer and cytotoxicity of a *Rubus longisepalus* var. tozawai (Nakai) T.B.Lee hexane extract, which is confirmed to have an excellent efficacy in Example 3.2, in cell models.

Figure 6:
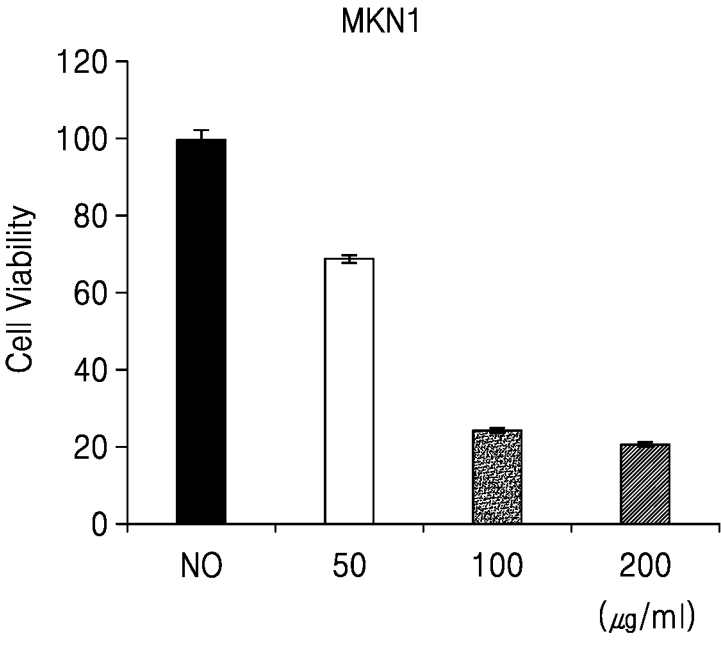
FIG. 6 shows diagrams confirming cell growth inhibitory ability of *Rubus longisepalus* var. tozawai (Nakai) T.B.Lee hexane extracts of each concentration on the diffuse-type gastric cancer cell lines.
Figure 6:
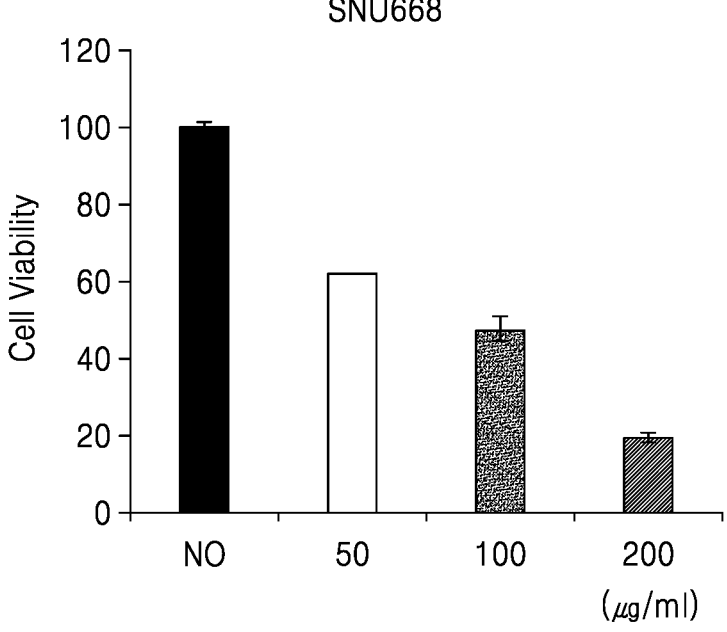

First, in order to evaluate anticancer efficacy against diffuse-type gastric cancer, *Rubus longisepalus* var. tozawai (Nakai) T.B.Lee hexane extracts of each concentration (50 µg/ml, 100 µg/ml, and 200 µg/ml) for each solvent were treated on MKN1 and SNU668, which are the diffuse-type gastric cancer cell lines selected in Example 1, and then the cell growth inhibitory ability was confirmed by an MTT assay. As a result, it was confirmed that a *Rubus longisepalus* var. tozawai (Nakai) T.B.Lee hexane extract is capable of strongly inhibiting growth of diffuse-type gastric cancer cells even at a low concentration of 50 µg/ml (FIG. 6).

Figure 7:
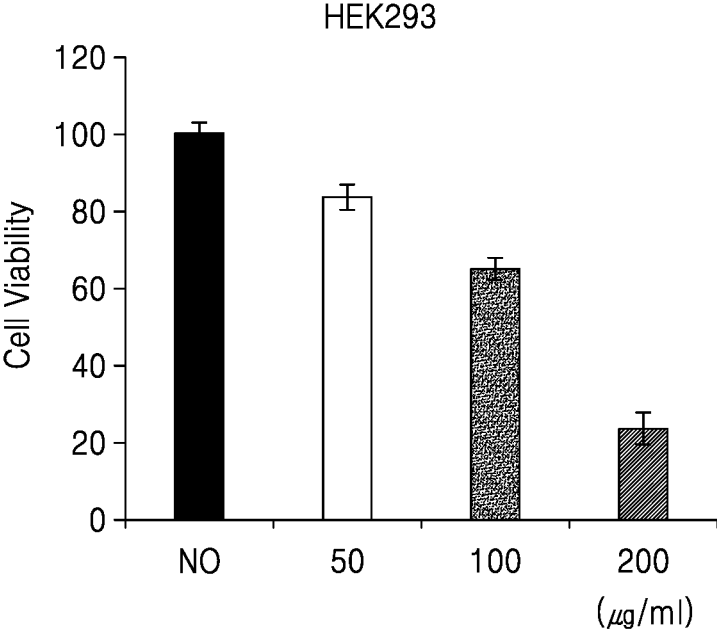
FIG. 7 shows a diagram confirming cell viability inhibitory ability of *Rubus longisepalus* var. tozawai (Nakai) T.B.Lee hexane extracts of each concentration on normal cell lines.
Figure 7:
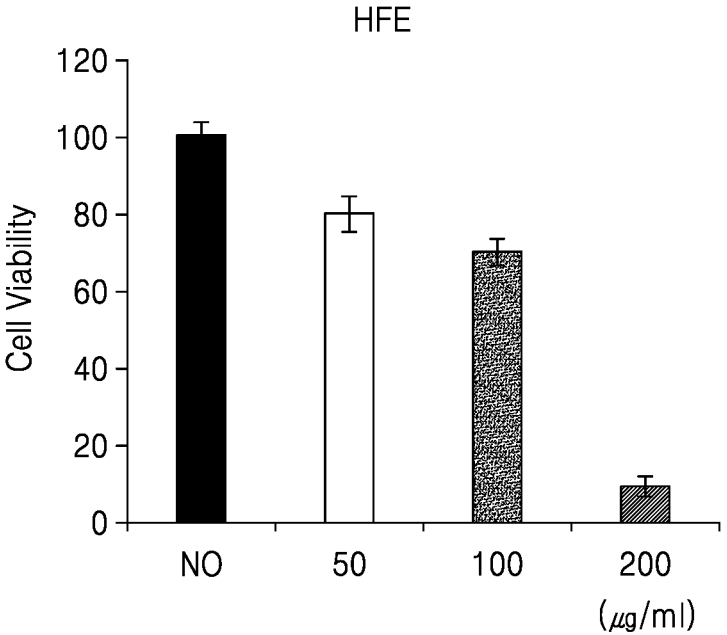

Next, in order to evaluate cytotoxicity to normal cell lines, *Rubus longisepalus* var. tozawai (Nakai) T.B.Lee hexane extracts of each concentration (50 µg/ml, 100 µg/ml, and 200 µg/ml) were treated to HEK293, normal kidney cells, and HFE-145, normal gastric epithelium cells, and then, cell growth inhibitory ability thereof was confirmed by an MTT assay. As a result, the *Rubus longisepalus* var. tozawai (Nakai) T.B.Lee extract did not significantly inhibit cell viability, even at a high concentration of about 100 µg/ml, and it was confirmed that its toxicity to normal cells is low (FIG. 7).

Based on the above results, it may be seen that a *Rubus longisepalus* var. tozawai (Nakai) T.B.Lee hexane extract has excellent anticancer efficacy for diffuse-type gastric cancer and low cytotoxicity to normal cells.

3.4 Evaluation of Treatment Efficacy for Diffuse-Type Gastric Cancer and Cytotoxicity of *Rubus longisepalus* Var. Tozawai (Nakai) T.B.Lee Hexane Extract-Organoid Models The following experiments were performed to evaluate a treatment efficacy for diffuse-type gastric cancer and cytotoxicity of a *Rubus longisepalus* var. tozawai (Nakai) T.B.Lee hexane extract, which is confirmed to have an excellent efficacy in Example 3.2, in organoid models.

Figure 8:
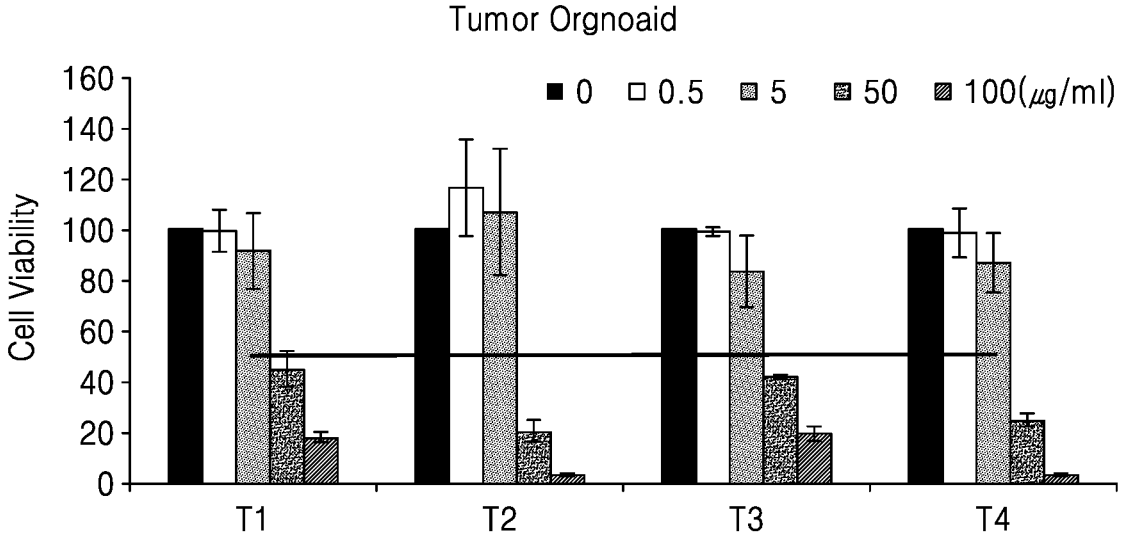
FIG. 8 shows diagrams confirming cell growth inhibitory ability of *Rubus longisepalus* var. tozawai (Nakai) T.B.Lee hexane extracts of each concentration on diffuse-type gastric cancer organoids.

First, in order to evaluate anticancer efficacy against diffuse-type gastric cancer organoids, *Rubus longisepalus* var. tozawai (Nakai) T.B.Lee hexane extracts of each concentrations (0.5 µg/ml, 5 g/ml, 50 µg/ml, and 100 µg/ml) were treated on an organoid library prepared from cancer tissues of 4 diffuse-type gastric cancer patients by the method described in Example 3.4, and cell growth inhibitory ability thereof was confirmed by an MTT assay. As a result, it was confirmed that the *Rubus longisepalus* var. tozawai (Nakai) T.B.Lee extracts showed an excellent inhibitory ability on all the diffuse-type gastric cancer organoids of 4 patients, even at a level of 50 µg/ml, and the extracts were capable of killing most of the cancer cells at a concentration of 100 µg/ml or higher (FIG. 8).

Figure 9:
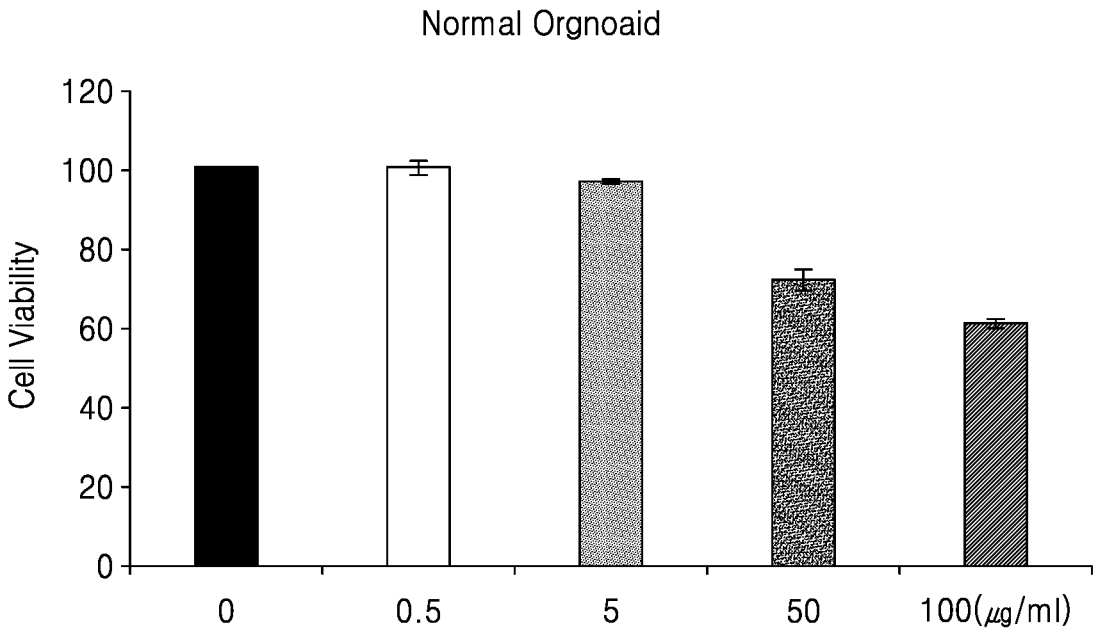
FIG. 9 shows a diagram confirming cell viability inhibitory ability of *Rubus longisepalus* var. tozawai (Nakai) T.B.Lee hexane extracts of each concentration on normal organoids.

Next, in order to evaluate cytotoxicity to a normal gastric organoid, *Rubus longisepalus* var. tozawai (Nakai) T.B.Lee extracts of each concentration (0.5 µg/ml, 5 µg/ml, 50 µg/ml, and 100 µg/ml) were treated to a organoid library prepared from a gastric tissue of a normal person, and then, cell viability inhibitory activity was confirmed by an MTT assay. As a result, it was confirmed that the *Rubus longisepalus* var. tozawai (Nakai) T.B.Lee extract showed cell viability of about 60% at a high concentration of 100 µg/ml, and the toxicity to normal tissues was confirmed to be low (FIG. 9).

Based on the above results, it may be seen that a *Rubus longisepalus* var. tozawai (Nakai) T.B.Lee hexane extract has excellent anticancer efficacy for diffuse-type gastric cancer and low cytotoxicity to normal cells.

3.5 Evaluation of Anticancer Efficacy of Extracts of *Rubus longisepalus* Var. Tozawai (Nakai) T.B.Lee and Other Plants Belonging to Genus *Rubus* on Various Cancers In order to compare and evaluate the anticancer efficacy of a *Rubus longisepalus* var. tozawai (Nakai) T.B.Lee extract with extracts of other plants belonging to the genus *Rubus*, such as *Rubus coreanus*, and *Rubus longisepalus* Nakai, the following experiment was performed.

Specifically, whole plants of *Rubus longisepalus* Nakai were collected from Geoje Island in August 2020, washed with water sufficiently, and dried with warm air (30° C. for 7 days to obtain 4.36 kg of dried plant. Thereafter, the dried plant was placed in a crusher and sliced to a size of 20 mm, and put into an extraction container, 43.6 L of 70% ethanol/water was added, the sample was stirred by shaking at room temperature for 7 days for an extraction, the process of gravity filtration by using a Whatman filter paper having a film thickness of 0.34 mm and a glass funnel was repeated twice ('extraction-filtration' twice) on the mixture to obtain a filtered extract. The filtered extract was transferred to a round flask, put in a low pressure evaporator, and concentrated by evaporating the solvent completely at 35° C. under reduced pressure to obtain 347.3 g of an ethanol extract of *Rubus longisepalus* Nakai (yield 8.0%). In addition, the hexane extract was obtained by the same method as the preparation method of the *Rubus longisepalus* var. tozawai (Nakai) T.B.Lee extract.

Next, for the *Rubus coreanus*, fruits of *Rubus coreanus* Miq. plants were purchased from 'Dusone Herb inc.' in 2016, crushed, and put in an extraction container, after adding 600 mL of ethanol, reflux extraction was performed for 2 hours, and the process of gravity filtration by using a Whatman filter paper having a film thickness of 0.34 mm and a glass funnel was repeated twice ('extraction-filtration' twice) on the mixture to obtain a filtered extract. The filtered extract was transferred to a round flask, put in a low pressure evaporator, and concentrated by evaporating the solvent completely at 35° C. under reduced pressure to obtain 9.8 g of a *Rubus coreanus* ethanol extract (Hereinafter referred to as '*Rubus coreanus*') (yield 16.3%). In addition, the hexane extract was obtained by the same method as the preparation method of the *Rubus longisepalus* var. tozawai (Nakai) T.B.Lee extract.

Next, extracts of *Rubus longisepalus* var. tozawai (Nakai) T.B.Lee, *Rubus coreanus*, and *Rubus longisepalus* Nakai of each concentration (50 µg/ml, 100 µg/ml, and 200 µg/ml) were treated on diffuse-type gastric cancer cell lines (MKN1 and SNU668), an intestinal-type gastric cancer cell line (MKN74), a prostate cancer cell line (DU145), and a colorectal cancer cell line (SNUC4), and then, cell viability inhibitory activity was confirmed by an MTT assay.

Figure 10:
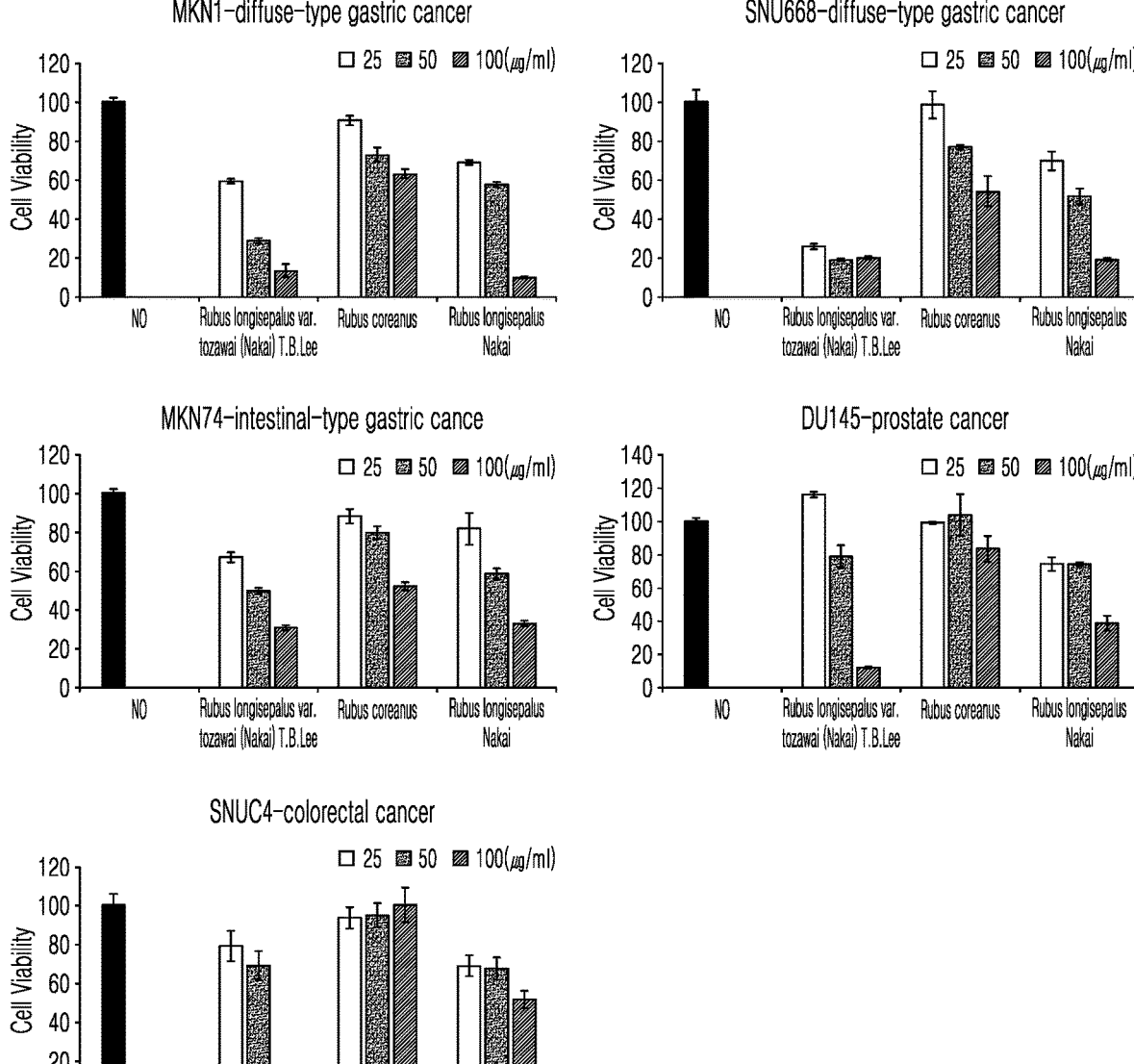
FIG. 10 shows a diagram confirming cell growth inhibitory abilities of hexane extracts of *Rubus longisepalus* var. tozawai (Nakai) T.B.Lee, *Rubus coreanus* Miq., or *Rubus longisepalus* Nakai against various cancers.

As a result, in the case of the diffuse-type gastric cancer, it was confirmed that the *Rubus longisepalus* var. tozawai (Nakai) T.B.Lee extract showed a significantly superior cancer cell suppression ability compared to the *Rubus coreanus* extract and the *Rubus longisepalus* Nakai extract at low concentrations of 25 µg/ml and 50 µg/ml, and the *Rubus longisepalus* var. tozawai (Nakai) T.B.Lee extract also exhibited an anticancer efficacy against intestinal-type gastric cancer, prostate cancer, and colorectal cancer (FIG. 10).

In particular, when comparing only the cases of diffuse-type gastric cancer and intestinal-type gastric cancer, it was confirmed that the cancer-suppressing ability was particularly strong in diffuse-type gastric cancer compared to intestinal-type gastric cancer.

Based on the above results, it may be seen that a *Rubus longisepalus* var. tozawai (Nakai) T.B.Lee extract has superior anticancer efficacy against various cancers compared to other plants belonging to the genus *Rubus*, and in particular, it may be seen that the anticancer efficacy against diffuse-type gastric cancer is more excellent.

The above description of the present disclosure is for illustrative purposes, and those skilled in the art to which the present disclosure belongs will be able to understand that the examples and embodiments can be easily modified without changing the technical idea or essential features of the disclosure. Therefore, it should be understood that the above examples are not limitative, but illustrative in all aspects.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A method of treating cancer, the method comprising administering a pharmaceutical composition comprising a *Rubus tozawae* Nakai ex J. Y. Yang extract or a fraction thereof to a subject.

2. The method of treating cancer of claim 1, wherein the extract is extracted by at least one solvent selected from water, methanol, ethanol, propanol, butanol, glycerin, butylene glycol, propylene glycol, methyl acetate, ethyl acetate, acetone, benzene, hexane, diethyl ether, and dichloromethane.

3. The method of treating cancer of claim 1, wherein the extract is extracted by at least one method selected from reduced pressure high temperature extraction, boiling extraction, reflux extraction, hot water extraction, cold extraction, room temperature extraction, ultrasonic extraction, steam extraction, and fractional extraction.

4. The method of treating cancer of claim 1, wherein the cancer is gastric cancer, liver cancer, lung cancer, pancreatic cancer, non-small cell lung cancer, colon cancer, bone cancer, skin cancer, head or neck cancer, skin or intraocular melanoma, uterine cancer, ovarian cancer, rectal cancer, colorectal cancer, perianal cancer, colon cancer, breast cancer, cervical cancer, fallopian tube carcinoma, endometrial carcinoma, vaginal carcinoma, vulvar carcinoma, Hodgkin's disease, esophageal cancer, small intestine cancer, adenocarcinoma of endocrine glands, thyroid cancer, parathyroid cancer, adrenal cancer, soft tissue sarcoma, urethral cancer, penile cancer, prostate cancer, chronic or acute leukemia, lymphocytic lymphoma, bladder cancer, kidney or ureter cancer, renal cell carcinoma, renal pelvic carcinoma, central nervous system (CNS) tumor, primary central nervous system lymphoma, spinal cord tumor, brainstem glioma, or pituitary adenoma.

5. The method of treating cancer of claim 1, wherein the cancer is diffuse-type gastric cancer.

* * * * *